United States Patent
Chelli

(10) Patent No.: US 11,806,455 B2
(45) Date of Patent: Nov. 7, 2023

(54) FLUID CONDUIT SYSTEM

(71) Applicant: Bellco S.R.L., Mirandola (IT)

(72) Inventor: Niccolo Chelli, Rufina (IT)

(73) Assignee: Bellco S.R.L., Mirandola (IT)

( * ) Notice: Subject to any disclaimer, the term of this patent is extended or adjusted under 35 U.S.C. 154(b) by 108 days.

(21) Appl. No.: 17/476,072

(22) Filed: Sep. 15, 2021

(65) Prior Publication Data
US 2023/0085348 A1   Mar. 16, 2023

(51) Int. Cl.
*A61M 1/16* (2006.01)
*A61M 39/08* (2006.01)

(52) U.S. Cl.
CPC ........ *A61M 1/1696* (2013.01); *A61M 1/1601* (2014.02); *A61M 39/08* (2013.01); *A61M 2039/087* (2013.01)

(58) Field of Classification Search
None
See application file for complete search history.

(56) References Cited

U.S. PATENT DOCUMENTS

| | | | | |
|---|---|---|---|---|
| 2,575,240 A * | 11/1951 | Thompson | ................ | F16K 7/07 251/5 |
| 4,195,810 A * | 4/1980 | Lavin | ....................... | F16K 7/07 251/5 |
| 5,241,968 A * | 9/1993 | Slater | ..................... | A61B 10/06 606/208 |
| 5,336,051 A * | 8/1994 | Tamari | ................ | A61M 1/3641 417/474 |
| 5,538,002 A * | 7/1996 | Boussignac | ......... | A61M 39/228 128/207.14 |
| 5,737,822 A * | 4/1998 | Driver | ................... | F16L 47/345 29/523 |
| 7,854,731 B2 * | 12/2010 | Rome | ............... | A61M 25/0097 604/247 |
| 2005/0021005 A1 | 1/2005 | Flaherty et al. | | |
| 2010/0274174 A1 | 10/2010 | Swisher | | |
| 2013/0310768 A1 * | 11/2013 | Ebara | .................. | A61M 39/284 604/250 |
| 2017/0281847 A1 | 10/2017 | Manda et al. | | |
| 2019/0049047 A1 * | 2/2019 | Cruson | ................... | F16L 33/08 |
| 2020/0008898 A1 | 1/2020 | Rousche et al. | | |

OTHER PUBLICATIONS

U.S. Appl. No. 17/191,395, filed Mar. 3, 2021, naming inventors Chelli et al.
U.S. Appl. No. 17/195,256, filed Mar. 8, 2021, naming inventors Chelli et al.
International Search Report and Written Opinion of International Application No. PCT/IB2022/060959 dated Feb. 14, 2023, 10 pp.

* cited by examiner

*Primary Examiner* — Krishnan S Menon
(74) *Attorney, Agent, or Firm* — Shumaker & Sieffert, P.A.

(57) ABSTRACT

In some examples, a conduit system includes a conduit defining a conduit lumen configured to provide a flow path for a fluid between a container and a medical machine. A flexible member secured to the conduit is configured to substantially occlude (e.g., close) the conduit lumen when deformed by a force acting on the flexible member toward the lumen. The conduit system includes a clamp head configured to pass through an opening defined by the conduit and exert the force on the flexible member, such that the flexible member occludes the conduit lumen. In examples, the conduit is substantially rigid conduit configured to provide a relatively constant geometry and/or flow path for the discharge of a nozzle.

20 Claims, 5 Drawing Sheets

FLUID CONDUIT SYSTEM

TECHNICAL FIELD

This disclosure is related to a fluid conduit system.

BACKGROUND

Dialysis machines may be used to remove waste products from blood of a patient when the kidneys of the patient are no longer able to adequately do so. During dialysis, the dialysis machine may generate or regenerate dialysate using specified concentrations of solute buffers, osmotic agents, cations, and other concentrates for biocompatibility with the patient. The dialysis machine may provide the dialysate to a cycler for delivery to the patient. The generation or regeneration of dialysate may require a patient or another user to control a fluid flow between external (e.g., disposable) elements and the dialysis machine.

SUMMARY

This disclosure describes a conduit system configured to provide a flow path for a material. The conduit system includes a conduit defining a conduit lumen configured to provide the flow path. The conduit includes a conduit wall defining an opening through the conduit wall and opening into the lumen. A flexible member secured to the conduit is configured to substantially occlude (e.g., close) the conduit lumen when deformed, e.g., by a clamping force exerted on the flexible member by a clamp head. The clamp head is configured to pass through the opening to exert the clamping force on the flexible member. In examples, the conduit system includes a venturi nozzle configured to mix a first material and a second material and discharge the mixture to the conduit lumen.

In an example, an apparatus comprises: a conduit comprising a conduit wall defining a conduit lumen, wherein the conduit wall defines an opening open to the conduit lumen; a flexible member secured to the conduit wall, wherein the flexible member covers the opening, and wherein the flexible member is configured to deform to occlude the conduit lumen when a clamping force in a direction toward conduit lumen is exerted on the flexible member; and a clamp head configured to pass through the opening to exert the clamping force on the flexible member.

In an example, a fluid delivery system comprises: a container defining a volume; a nozzle defining a nozzle throat in fluid communication with the volume; a conduit comprising a conduit wall defining a conduit lumen extending from a conduit inlet to a conduit outlet, wherein the nozzle throat is in fluid communication with the conduit inlet, and wherein the conduit wall defines an opening open to the conduit lumen; a flexible member secured to the conduit wall, wherein the flexible member covers the opening, and wherein the flexible member is configured to deform to occlude the conduit lumen; and a clamp head configured to pass through the opening to exert a clamping force on the flexible member to cause the flexible member to deform to occlude the conduit lumen, wherein the conduit includes a rigid body configured such that the conduit inlet, the conduit outlet, and the conduit wall defining the opening are substantially stationary with respect to each other when the clamp head exerts the clamping force on the flexible member.

In an example, a method comprises: displacing a clamp head through an opening defined by a conduit wall of a conduit, wherein the conduit wall defines a conduit lumen and the opening opens into the conduit lumen; exerting a clamping force on a flexible member covering the opening using the clamp head displaced through the opening, the clamping force being sufficient to deform the flexible member to occlude the conduit lumen.

The details of one or more examples are set forth in the accompanying drawings and the description below. Other features, objects, and advantages will be apparent from the description and drawings, and from the claims.

DETAILED DESCRIPTION

Figure 1:
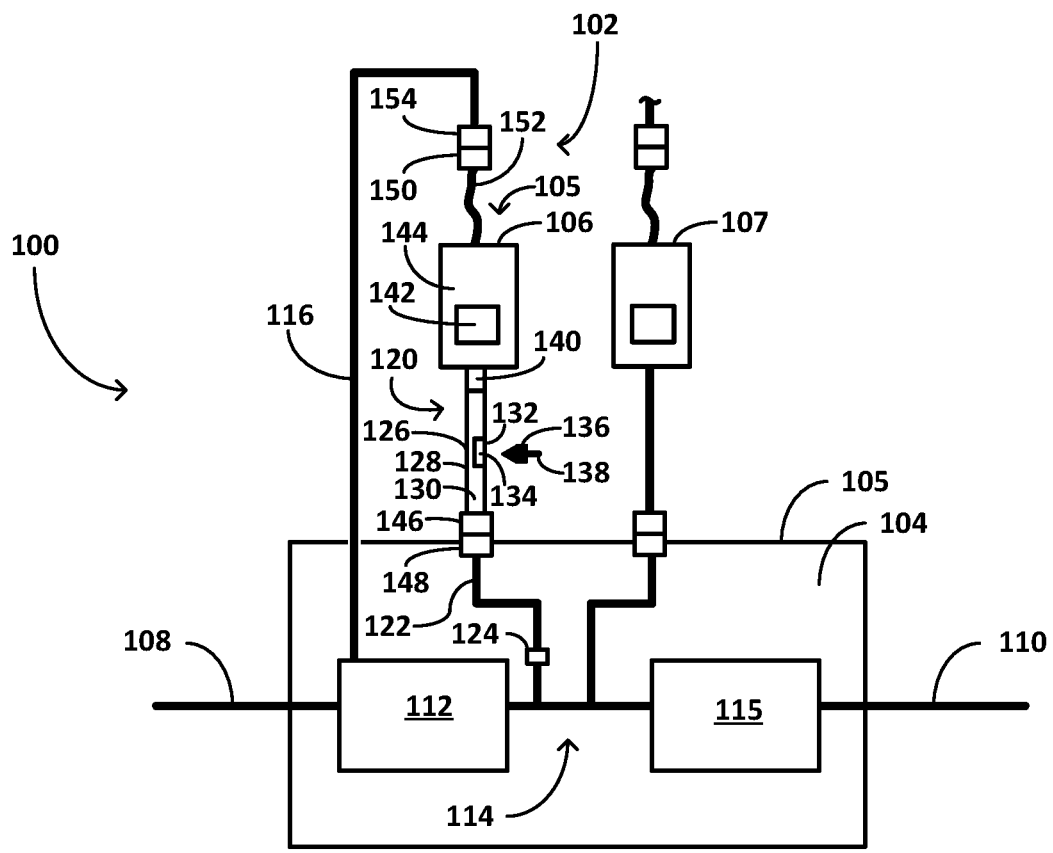
FIG. 1 is a conceptual diagram illustrating an example medical system configured to deliver a medical fluid such as dialysate.

This disclosure describes a conduit configured to establish a connection between a medical machine and a container, or between other two components. In some examples, the conduit is configured to provide a connection between a materials source, such as a medical container (e.g., a bag) holding a medical material (e.g., in a solid and/or a liquid state), and a medical machine configured to utilize the medical material to provide therapy to a patient. The conduit defines a conduit lumen configured to provide a flow path between the materials source and the medical machine. A flexible member secured to the conduit is configured to substantially occlude the conduit lumen (e.g., close to fully block fluid flow through the conduit or block fluid flow through the conduit to an insignificant flow rate) when deformed by a force acting on the flexible member in a direction toward the conduit lumen. The conduit system includes a clamp head configured to pass through an opening defined by the conduit and exert the force on the flexible member, such that the flexible member occludes the conduit lumen to control and/or substantially cease (e.g., cease or nearly cease to the extent permitted by manufacturing tolerances) a flow of material between the medical container and the medical machine.

The conduit system may be configured to control (e.g., substantially cease) a flow in systems involving pharmacological preparation and delivery to a patient. The conduit system may be advantageous when a procedure requires the patient or another user (e.g., a patient caretaker or clinician) to cease a flow between a container, such as a disposable concentrate bag, and a medical machine, such as a dialysis machine. For example, the conduit system may be utilized to substantially cease (e.g., cease or nearly cease to flow to an insignificant flow rate) a flow of dialysate or other fluid during or at the conclusion of a dialysis treatment. In examples, the conduit system includes a positioning member (e.g., a squeeze handle) operable by a patient or other user, or automatically by a device, to cause the clamp head to exert the clamping force on the flexible member to control the flow. The conduit system may be configured to reduce or even prevent continued flow of the fluid when the flexible member occludes the conduit lumen, such that any unused fluid remains within the container. In examples, the conduit system is secured to the container and configured to be disposed of with the container.

The conduit system may have particular advantages when utilized in home therapy delivery systems such as home dialysis systems. For example, the conduit system may enable the patient or another user to substantially prevent (e.g., prevent or nearly prevent) a flow of fluid from the container (e.g., a medical bag) to, for example, dispose of the container while substantially retaining any unused fluid within the container (e.g., at the conclusion of a dialysis treatment, or when the container is replaced during a dialysis treatment). The conduit system may enable the patient or another user to commence a fluid flow from the container following, for example, an initial fill of the container. In some examples, the conduit system includes control circuitry configured to control the clamp head to apply a force to the flexible member to substantially cease and/or prevent a fluid flow from the container in response to a control signal communicated from instrumentation within a dialysis system, such as a control signal indicating a predetermined out-of-range parameter (e.g., a conductivity, pH, air presence, or another monitored parameter). In addition, in some examples, the control circuitry is configured to control the clamp head to release the force applied to the flexible material to commence a fluid flow from the container based on a control signal received from a dialysis system (e.g., at the commencement of a dialysis treatment, and/or following a replacement of the container).

In examples, the conduit system includes a nozzle configured to mix a solid concentrate within the container and a fluid (e.g., purified water) added to the container (e.g., from a dialysis system), such the container may be shipped to a patient and/or treatment site substantially holding only dry contents.

In examples, the conduit system is configured to provide a fluid connection between a container holding one or more materials and the medical machine. The conduit system may be configured to generate a mixture including the one or more materials before providing the mixture to the medical machine. For example, a container may be configured to hold a concentrate and receive a liquid solvent (e.g., purified water) from the conduit system. The conduit system may be configured to deliver the liquid solvent (e.g., from a medical machine) to the container to generate a mixture of the concentrate and the liquid solvent (e.g., within the container). The conduit system may be configured to provide the thus-generated mixture to the medical machine. In examples, the conduit system includes a nozzle (e.g., a venturi nozzle) configured to deliver the liquid solvent to the container to mix the concentrate and the solvent. The nozzle may be configured to enhance the mixing process, such that, for example, liquid solvent discharged from the nozzle into the container generates a substantially homogenous mixture of the concentrate and the solvent. For example, the nozzle may be configured to enhance dissolution of a solid concentrate within the liquid solvent to generate the substantially homogenous mixture.

In some examples, a container may be configured to hold a concentrate (e.g., a dialysate concentrate) and a liquid solvent (e.g., purified water) in segregated compartments. The conduit system may be configured to receive the concentrate and liquid solvent from the container and mix the concentrate and the liquid solvent before providing the mixture to the medical machine. The nozzle may be configured to mix the concentrate and the solvent. The nozzle may be configured to discharge the mixture to the conduit lumen, such that the conduit may provide the mixture to the medical machine. In examples, the nozzle is configured to receive a flow of material (e.g., solid or liquid) at one or more nozzle inlets and discharge the flow of material to the conduit lumen through a nozzle outlet.

The conduit may be configured to receive the flow of material from the nozzle outlet and provide the flow of material to the medical machine via the conduit lumen. In some examples, the conduit is configured as a substantially rigid conduit (e.g., unable to bend or be forced out of shape without adversely impacting the structural integrity of the conduit). In examples, the substantially rigid conduit is configured to substantially maintain an orientation of the nozzle with respect to the conduit such that, for example, when the nozzle provides an inlet jet of solvent to the container, the orientation of the nozzle more effectively directs the inlet jet into a volume defined by the container (e.g., a volume holding the concentrate) and limits impacts of the inlet jet with one or more sides of the container defining the volume. In examples, the substantially rigid conduit is configured to assist a flow symmetry of the inlet jet within the volume to enhance dissolution of the concentrate and mixing within the liquid solvent. For example, when the container is configured to hang from a top of the container and the conduit system is configured to discharge a liquid solvent vertically into the volume defined by the container, the substantially rigid conduit may be configured to assist in substantially maintaining the inlet jet of the nozzle in a substantially vertical orientation relative to the container.

In examples, the substantially rigid conduit is configured to provide a relatively constant geometry and/or flow path when the nozzle discharges a fluid from the container to the conduit lumen. The relatively constant geometry and/or flow path at the discharge of the nozzle may help ensure the mixture provided by the nozzle (e.g., from the container) is adequately mixed. For example, the substantially rigid conduit may minimize and/or eliminate unanticipated flow restrictions caused by bending and/or kinking that might occur with a substantially flexible conduit, such as flexible tubing. The substantially rigid conduit may define the opening through which the clamp head passes when the clamp head acts to deform the flexible member to substantially occlude the conduit lumen.

In examples, the conduit lumen is configured to provide a flow path via the conduit lumen from an inlet of the conduit ("conduit inlet") to an outlet of the conduit ("conduit outlet") (e.g., when the conduit system provides a flow from a container to a medical machine). The conduit lumen may be configured to provide the flow path from the conduit outlet to the conduit inlet (e.g., when the conduit system provides a flow from a medical machine to a container). In examples, the conduit includes a conduit wall substantially surrounding the lumen. The conduit wall may include an interior surface defining the lumen and an exterior surface opposite the inner surface. The conduit wall may define the opening covered by the flexible member. The flexible member may be configured to substantially block (e.g., fully block or nearly fully block to the extent permitted by manufacturing tolerances) fluid flow through the opening. The clamp head is configured to pass through the opening from the exterior surface to the interior surface to deform the flexible member.

The flexible member covers the opening, such that when the clamp head exerts the clamping force on the flexible member, the flexible member deforms (e.g., stretches) toward the conduit lumen to occlude the flow path. In examples, the flexible member is secured to the interior surface of the conduit wall. In other examples, the flexible member is secured to an outer surface of the conduit wall. In examples, the conduit wall defines a rigid body configured such that the conduit inlet, the conduit outlet, and the opening are substantially stationary with respect to each other when the clamp head exerts the clamping force to deform the flexible member.

The flexible member may be configured to fluidly communicate with a fluid in the flow path provided by the conduit lumen. In examples, the flexible member is configured to define at least some portion of flow area defined within the flow path, such that when the clamp head causes the flexible member to deform inward, the flexible member decreases the flow area to occlude the flow path. In examples, the flexible member includes a member body defining a member lumen. For example, the flexible member may be in the form of a flexible tubular body. In some examples, the flexible member is secured to the interior surface of the conduit such that the flow path from the conduit inlet to the conduit outlet passes through the member lumen, such that the member lumen defines the flow area. The clamp head may be configured to pass through the opening to exert a clamping force on the flexible member, causing the flexible member to deform inwardly and decrease and/or substantially close the flow area. In other examples, the flexible member may be secured to the exterior surface of the conduit and/or may not define a lumen.

In some examples, the conduit defines only one opening. In other examples, the conduit defines more than one opening, such as a first opening and a second opening. The conduit system may include a first clamp head configured to pass through the first opening and a second clamp head configured to pass through the second opening. The flexible member may be configured to cover the first opening and the second opening. For example, the same piece of flexible member can cover the first and second openings or physical separate pieces of flexible member can cover respective ones of the first and second openings. In examples, such as some examples in which the conduit includes only one opening, a clamp head includes a clamp face defining a surface configured to substantially conform with an interior surface of the conduit such that, for example, the clamp face may substantially deform the flexible member into conformance with the interior surface of the conduit to decrease and/or close off the flow area. In examples, the clamp face substantially conforms with the interior surface such that the clamp face exerts a substantially uniform force profile over a portion of the flexible member compressed between the clamp face and the interior surface.

The first clamp head may be configured to exert a first clamping force on the flexible member when the first clamp head passes through the first opening. If present, the second clamp head may be configured to exert a second clamping force on the flexible member when the second clamp head passes through the second opening. In examples, the first clamping force may act in a first direction opposite a direction of the second clamping force, such that the first and second clamping force tend to substantially squeeze the member body defined by the flexible member (e.g., to substantially "clamp-off" or "pinch-off" the member lumen) to cause the occlusion of the flow path from the conduit inlet to the conduit outlet. In examples, a positioning member of the conduit system (e.g., a positioning member operable by a patient or another user) is configured to cause the first clamp head to exert the first clamping force and cause the second clamp head to exert the second clamping force. In some examples, the first clamp head includes a first clamp face and the second clamp head includes a second clamp face, and the first clamp face is configured to substantially conform to the second clamp face when the first clamp head and the second clamp substantially squeeze the member body defined by the flexible member to decrease and/or substantially close the flow area. In examples, the first clamp face substantially conforms to the second clamp face such that the first clamp face and second clamp face together exert a substantially uniform force profile over a portion of the flexible member compressed between the first clamp face and the second clamp face.

In some examples, the conduit system includes a container (e.g., a medical bag) configured to hold the material to be delivered to the medical machine. A nozzle may be secured to the container in some examples. The conduit system may be configured such that the nozzle inlet is in fluid communication with one or more volumes defined by the container, with the one or more volumes each configured to hold a material. In examples, the container defines a first volume configured to hold a first material (e.g., a solid dialysate concentrate) and a second volume configured to hold a second material (e.g., purified water) different from the first material. The nozzle (e.g., a venturi nozzle) may be secured to the container such that a first nozzle inlet receives the first material and a second nozzle inlet receives the second material. The nozzle may be configured to provide a mixture of the first material and the second material to the conduit lumen via the conduit inlet, such that the conduit may provide the mixture to a medical machine via the conduit outlet.

The conduit may include a connector defining the conduit outlet and configured to mechanically engage a second conduit, such as a line (e.g., a fluid line) within a medical machine ("machine line"). The connector may be configured to mechanically engage the second conduit to fluidly connect the conduit outlet and the second conduit. The connector may be configured such that, when the connector mechanically couples with the second conduit, the connector establishes a flow path from the one or more nozzle inlets to a lumen of the second conduit. In some examples, the connector is configured to insert into a socket to mechanically engage the second conduit, or the second conduit can define the socket. In some examples, a medical machine (e.g., a dialysis machine) mechanically supports the second conduit. In examples, the connector is configured to mechanically disengage from the second conduit. Hence, the connector may be configured such that a user (e.g., a patient, patient caretaker, or clinician) may translate the connector toward the second conduit to mechanically couple the connector and the second conduit (e.g., a machine line within a medical machine), such that the medical machine may utilize a medical material within the container to provide therapy to the patient. The connector may be configured such that a user (e.g., a patient, patient caretaker, or clinician) may translate the connector away from the second conduit to mechanically disengage the connector and the second conduit when material delivery to the medical machine is no longer required, such as at the conclusion of a medical treatment.

FIG. 1 is a block diagram illustrating an example medical system 100 using an example fluid delivery system 102.

Medical system 100 includes a medical machine 104 configured to produce a medication (e.g., a medical solution) for a patient therapy (e.g., dialysis) using one or more concentrates. For example, medical machine 104 may be configured to produce dialysate for the patient using concentrates contained in one or more containers such as containers 106, 107. For example, medical system 100 may be configured to generate the medication by at least mixing a concentrate within container 106 with a fluid such as water. In examples, medical system 100 is configured to receive the fluid via fluid line 108 and deliver the medication produced (e.g., dialysate) via an infusion line 110. For example, infusion line 110 may provide dialysate to a cycler configured to provide therapy to a patient using the dialysate, or to a container configured to retain the dialysate for subsequent use.

Medical system 100 may include a conditioning system 112 configured to provide fluid received via fluid line 108 to a generation flow path 114 defined by medical machine 104. Conditioning system 112 may include, for example, a pump configured to provide a motive force to the fluid received via fluid line 108 to drive the fluid through generation flow path 114. In some examples, conditioning system 112 may include one or more filters and/or sorbent cartridges configured to remove impurities (e.g., particulate matter and/or ions) from the fluid prior to the fluid entering generation flow path 114. In addition, in some examples, conditioning system 112 may include one or more sensors, such as a conductivity sensor and/or a pressure sensor, configured to monitor a physical state or condition of the fluid prior to the fluid entering generation flow path 114. In examples, conditioning system 112 includes a degasser configured to degas the fluid prior to entering generation flow path 114. The degasser may include, for example, a vacuum pump configured to create a vacuum to remove air and other gases from the fluid prior to entering generation flow path 114.

Medical system 100 may be configured to generate a medication using the one or more concentrates held in one or more containers such as container 106 and container 107. In examples, medical system 100 may be configured to provide a fluid (e.g., purified water) to a container system 105 including container 106 such that container system 105 may generate a solution (e.g., a medical solution). For example, medical system 100 may be configured to receive a fluid (e.g., the medical solution) from container 106 via conduit system 120 and provide the fluid to generation flow path 114 using a machine fluid line 122. In some examples, container system 105 may be configured to utilize a single fluid path for both an injection of fluid (e.g., purified water) into container system 105 and extraction of a medical solution. For example, container system 105 may be configured to receive the fluid via machine fluid line 122 and conduit system 120 in a first flow direction to generate a medical solution, and then supply the medical solution via conduit system 120 and machine fluid line 122 in a second flow direction opposite the first flow direction.

In some examples, medical system 100 includes one or more pumps such as pump 124 configured to inject a solution from container 106 into generation flow path 114 via machine fluid line 122. In some examples, medical system 100 may include one or more additional filters (not shown) configured to filter the solution provided from container 106 prior to the concentrate solution entering generation flow path 114. The solution may include one or more solutes. In examples, the solute includes an osmotic agent such as glucose, dextrin, and/or icodextrin. In examples, the solute includes an ion such as sodium chloride, sodium lactate, magnesium chloride, calcium chloride, potassium chloride, and/or sodium bicarbonate. In examples, medical system 100 includes a mixing system 115 configured to monitor and/or further mix a medical fluid produced in generation flow path 114. Mixing system 115 may be configured to provide the medical fluid to infusion line 110. Mixing system 115 may include one or more sensors configured to evaluate one or more physical characteristics of the medical fluid, such as one or more of conductivity sensors, pH sensors, pressure sensors, flow sensors, or the like. In some examples, mixing system 115 includes one or more sterilization units, such as one or more ultrafilters, microbial filters, UV light sources, or other sterilization units configured to substantially sterilize dialysate prior to infusion into a patient.

Conduit system 120 includes a conduit 126 defining a conduit wall 128. Conduit wall 128 defines a conduit lumen 130. Conduit lumen 130 may be configured to provide a flow path for a fluid (e.g., a medical solution) from container 106 to machine fluid line 122. Conduit lumen 130 may be configured to provide a flow path for a fluid (e.g., purified water) from machine fluid line 122 to container 106. Conduit 126 defines an opening 132 extending through conduit wall 128 and opening into conduit lumen 130. Conduit system 120 includes a flexible member 134 covering opening 132. In examples, flexible member 134 is secured to an interior surface of conduit wall 128 to cover opening 132. In other examples, flexible member 134 is secured to an exterior surface of conduit wall 128 to cover opening 132. As used herein, when flexible member 134 covers opening 132, this may mean that flexible member 134 is configured to substantially prevent (e.g., prevent or nearly prevent to the extent permitted by manufacturing tolerances) a fluid flow passing through opening 132 and into conduit lumen 130. Thus, flexible member 134 is formed from a material that is configured to block fluid flow through the material. In some examples, flexible member 134 is formed from or otherwise includes silicone. In examples, flexible member 134 is formed from or otherwise includes a biocompatible deformable material. The biocompatible deformable material may be a material configured such that the material does not release any particulates due to frictional or thermal corrosion of the material.

Flexible member 134 is configured to substantially occlude a flow path within conduit lumen 130 when deformed by a force acting on flexible member 134 toward conduit lumen 130. The force acting on flexible member 134 may be a force in a substantially radial direction of conduit 126 (e.g., in a direction substantially orthogonal to a central longitudinal axis of conduit 126). Flexible member 134 may be configured to reduce and/or prevent flow of a fluid through conduit lumen 130. For example, flexible member 134 may be configured to reduce and/or prevent flow of a fluid (e.g., a medical solution) from container 106 to machine fluid line 122 when flexible member 134 occludes conduit lumen 130. Flexible member 134 may be configured to reduce and/or prevent flow of a fluid (e.g., purified water) from machine fluid line 122 to container 106 when flexible member 134 occludes conduit lumen 130. In examples, flexible member 134 is configured to fluidly communicate with the fluid flowing through conduit lumen 130. Flexible member 134 may be configured to define at least some portion of flow area defined within conduit lumen 130, such that when flexible member 134 deforms (e.g., deforms inwardly into conduit lumen 130), flexible member 134 decreases the flow area to occlude the flow path within conduit lumen 130. In some examples, flexible member 134 defines a member lumen and is configured such that the fluid flowing from container 106 to machine fluid line 122 flows through the member lumen. The member lumen may define the flow area. Flexible member 134 may be configured to reduce and, in some examples, close, the flow area defined by the member lumen when deformed inwardly into conduit lumen 130 to substantially occlude conduit lumen 130.

Conduit system 120 further includes a clamp head 136 configured to exert a clamping force on flexible member 134 to cause flexible member 134 to deform and substantially occlude conduit lumen 130. In examples, clamp head 136 is positioned substantially outside conduit 126 when in a first position relative to flexible member 134, in which flexible member 134 is not deformed and occluding conduit lumen 130. Clamp head 136 is configured to move from the first position to a second position in which flexible member 134 is deformed and occluding conduit lumen 130 by at least passing through conduit wall 128 via opening 132 to exert the clamping force on flexible member 134. In examples, clamp head 136 is configured to exert the clamping force in a direction toward conduit lumen 130 (e.g., in a direction substantially orthogonal to a central longitudinal axis of conduit 126). Clamp head 136 may be configured to contact flexible member 134 and exert the clamping force to cause flexible member 134 to deform inwardly into conduit lumen 130.

Clamp head 136 is configured to move between the first and second positions using any suitable technique. In some examples, conduit system 120 includes a positioning member 138 configured to cause clamp head 136 to move to the second position in which clamp head 136 exerts the clamping force on flexible member 134. In some examples, positioning member 138 is configured to be operable by a patient using medical machine 104 or another user assisting the patient, such that the patient or other user may control a flow of the fluid from container 106 to machine fluid line 122. In other examples, medical machine 104 includes control circuitry configured to automatically control positioning member 138 to move clamp head 136 between the first and second positions.

Conduit system 120 may include a nozzle 140 (e.g., a venturi nozzle). In examples, nozzle 140 is configured to receive a fluid from conduit lumen 130 (e.g., purified water or another solvent) and provide the fluid to container 106. Nozzle 140 may be configured to deliver the fluid to container 106 to generate a mixture of a solid and/or liquid concentrate and the liquid within container 106. Nozzle 140 may be configured to subsequently provide the thus-generated mixture from container 106 to conduit lumen 130. Nozzle 140 may be configured to enhance the mixing process, such that, for example, the fluid discharged from nozzle 140 into container 106 generates a substantially homogenous mixture of the concentrate and the fluid. For example, nozzle 140 may be configured to enhance dissolution of a solid concentrate within the liquid to generate the substantially homogenous mixture. Conduit 126 may be a substantially rigid conduit configured to substantially maintain an orientation of nozzle 140 with respect to conduit 126 such that, for example, the orientation of nozzle 140 more effectively directs an inlet jet of fluid into a volume defined by container 106 to assist a flow symmetry of the inlet jet within container 106.

In examples, nozzle 140 is configured to receive a first material (e.g., a solid dialysate concentrate) and a second material (e.g., purified water) from container 106 and mix the first material and the second material. For example, container 106 may define a first volume 142 configured to supply the first material to nozzle 140 and a second volume 144 configured to supply the second material to nozzle 140. Nozzle 140 may be configured to provide mixture of the first material and the second material to conduit lumen 130. Conduit 126 may be configured as a substantially rigid conduit in order to provide a relatively constant geometry and/or flow path for the discharge of nozzle 140 to, for example, help ensure the mixture provided by the nozzle is adequately mixed.

In some examples, conduit 126 includes a connector 146 configured to fluidically couple conduit lumen 130 and machine fluid line 122. Connector 146 is configured to mechanically engage machine fluid line 122 and/or some portion of medical machine 104 to fluidically couple conduit lumen 130 and machine fluid line 122. In examples, connector 146 is configured to engage a machine connector 148 mechanically supported by medical machine 104 (e.g., a housing of medical machine 104) to fluidically couple conduit lumen 130 and machine fluid line 122. Connector 146 may be configured to mechanically disengage from machine connector 148 to, for example, separate conduit system 120 and medical machine 104.

In examples, container system 105 may include a fluid connector 150 configured to fluidically couple machine fluid line 116 and container 106 (e.g., via a container inlet line 152). Fluid connector 150 may be configured to mechanically engage a fluid line connector 154 to fluidically couple machine fluid line 116 and container 106. Fluid connector 150 may be configured to mechanically disengage from fluid line connector 154. Fluid connector 150 may be configured to mechanically disengage from fluid line connector 154 to, for example, separate container system 105 and machine fluid line 116. In examples, container system 105 includes fluid connector 150, container 106, conduit system 120, and connector 146 as a substantially integrated unit, such that fluid connector 150, container 106, conduit system 120, and connector 146 may be mechanically disengaged from medical machine 104 for disposal or other reasons.

Hence, conduit system 120 may be configured to fluidically couple container 106 and machine fluid line 108, such that medical system 100 may produce a medication (e.g., dialysate) using one or more concentrates delivered from container 106 via conduit system 120. Conduit system 120 is configured to control (e.g., reduce and/or cease) a flow of the concentrate through conduit 126 using flexible member 134 and clamp head 136. In examples, conduit system 120 includes nozzle 140 configured to receive a first material (e.g., a solid dialysate concentrate) and a second material (e.g., purified water) from container 106 and mix the first material and second material to produce the concentrate. Conduit 126 may be a substantially rigid conduit in order to provide a relatively constant geometry and/or flow path for the discharge of nozzle 140 to, for example, help ensure the concentrate provided by the nozzle is adequately mixed.

Figure 2:
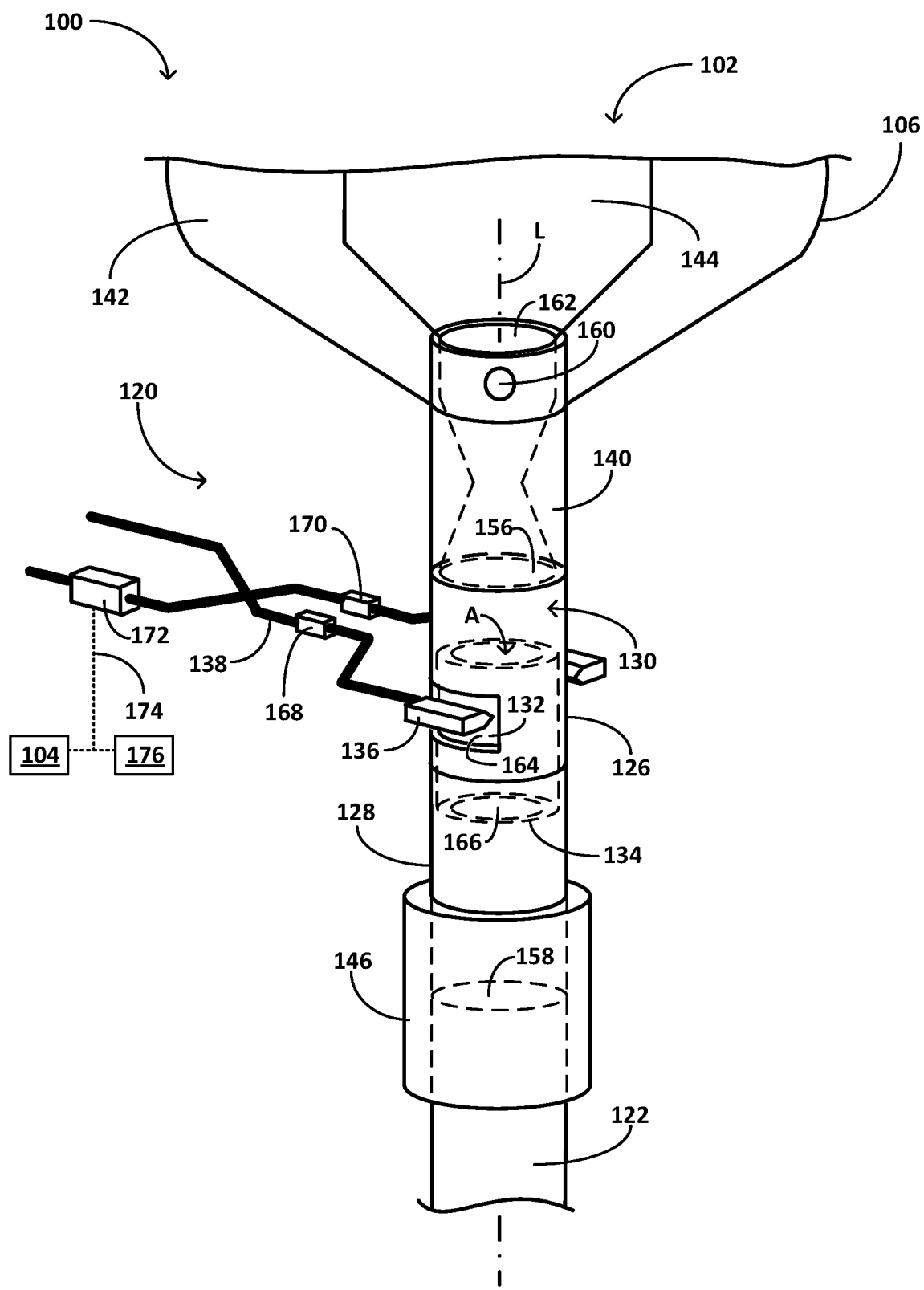
FIG. 2 is a conceptual diagram of an example conduit system including a conduit and a clamp head.
Figure 3:
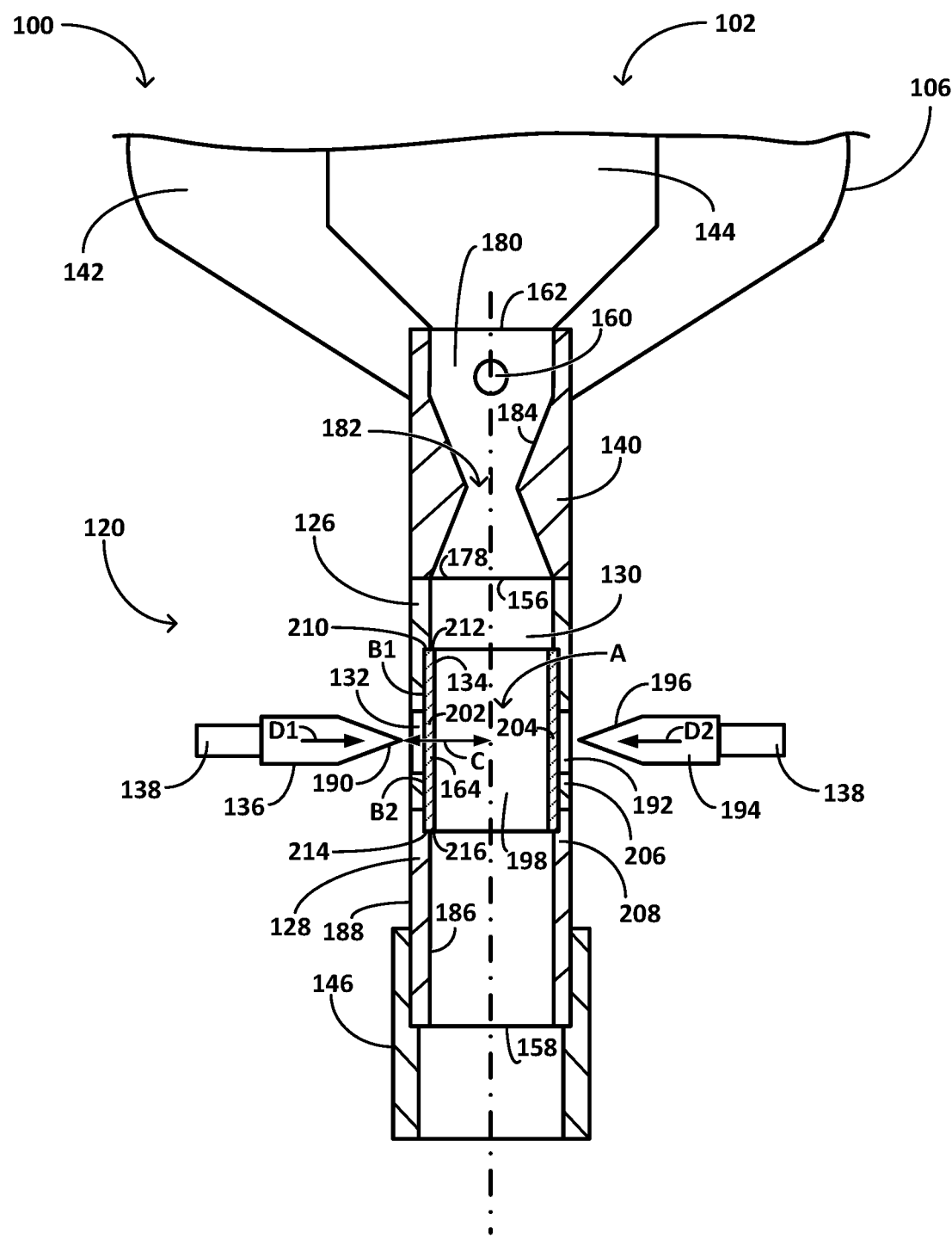
FIG. 3 is a conceptual diagram illustrating a cross-section of the conduit system of FIG. 2 with the clamp head in a first position, the cross-section being taken through a central longitudinal axis of the conduit.

FIG. 2 illustrates an example conduit system 120 including conduit 126 defining conduit lumen 130 and opening 132 extending through conduit wall 128 and opening to conduit lumen 130. FIG. 3 illustrates a cross-section of conduit system 120 with the cutting plane parallel to the page and through a central longitudinal axis L of conduit system 120.

Conduit system 120 is configured to provide a flow path for a fluid from container 106 to machine fluid line 122 via conduit lumen 130. Conduit lumen 130 is configured to define at least a portion of the flow path from container 106 to machine fluid line 122. In examples, conduit 126 defines a conduit inlet 156 opening to conduit lumen 130 and a conduit outlet 158 opening to conduit lumen 130. Conduit inlet 156 is fluidically coupled to conduit outlet 158 via conduit lumen 130.

Flexible member 134 is secured within conduit lumen 130 and configured to cover opening 132 defined by conduit 126. Clamp head 136 is configured to pass through opening 132 to exert a clamping force on flexible member 134, causing flexible member 134 to deform inwardly into conduit lumen 130 (e.g., toward central longitudinal axis L) to occlude conduit lumen 130. In examples, a boundary of opening 132 defines a specific shape (e.g., curvilinear, polygonal, or another shape), and clamp head 136 is configured to pass the through the specifically shaped boundary. In some examples, clamp head 136 defines a clamp head perimeter around clamp head 136, and the clamp head perimeter defines a shape substantially similar to the specific shape defined by the boundary of opening 132.

In examples, flexible member 134 defines a flow area A in the flow path provided by conduit lumen 130. In examples, flow area A is an area defined within conduit lumen 130. Conduit system 120 may be configured such that at least some portion of a fluid flow from conduit inlet 156 to conduit outlet 158 flows through flow area A. In examples, flow area A is a cross-sectional area (e.g., an area substantially perpendicular to central longitudinal axis L) defined by conduit 126 and/or flexible member 134. Flexible member 134 may be configured to reduce and/or close the flow area A when flexible member 134 deforms into conduit lumen 130, such that the deformation of flexible member 134 by clamp head 136 may reduce and/or close flow area A to control the flow from container 106 to machine fluid line 122. In examples, flexible member 134 includes a body 164 ("member body 164") configured to deform inwardly into conduit lumen 130 (e.g., toward central longitudinal axis L) to occlude conduit lumen 130 when clamp head 136 exerts the clamping force on member body 164.

Flexible member 134 may be a substantially elastic material, such that flexible member 134 deforms from an initial shape when clamp head 136 exerts the clamping force, and substantially returns to the initial shape when the clamping force is removed (e.g., when clamp head 136 is withdrawn back through opening 132). Thus, when clamp head 136 removes the clamping force from flexible member 134, flexible member 134 returns to a configuration that enables fluid flow through conduit lumen 130 from conduit inlet 156 to conduit outlet 158.

Flexible member 134 may be configured to cover opening 132. Flexible member 134 may be formed from a material that is substantially impermeable to fluids to help prevent a flow of a fluid from conduit lumen 130 through opening 132. In examples, flexible member 134 is configured to substantially prevent the fluid flow from conduit lumen 130 in an undeformed state (e.g., when clamp head 136 is not exerting a force on flexible member 134) and in a deformed state (e.g., when clamp head 136 exerts a force on flexible member 134). Flexible member 134 may have define shape sufficient to cover opening 132 to prevent a flow of fluid from conduit lumen 130 through opening 132. For example, flexible member 134 may define a substantially planar and/or curved body (e.g., a planar and/or curved body secured to an interior surface and/or exterior surface of conduit 126). Flexible member 134 may be configured to extend longitudinally over some portion or substantially all of a length defined by conduit 126 (e.g., a length parallel to central longitudinal axis L). In some examples, flexible member 134 extends longitudinally over only a portion of the length defined by conduit 126 (e.g., over a portion sufficient to cover opening 132). In some examples, flexible member 134 extends longitudinally over substantially all of the length defined by conduit 126.

In some examples, flexible member 134 is a substantially tubular body defining a member lumen 198. Flexible member 134 may be secured to an interior surface of conduit 126 such that member lumen 198 substantially defines the flow area A. Flexible member 134 may be configured to deform to reduce and/or close the flow area A when clamp head 136 passes through opening 132 and exerts the clamping force on flexible member 134. In examples, flow area A defines an area having a closed boundary. Conduit system 120 may be configured such that a flow of a fluid from conduit inlet 156 to conduit outlet 158 passes through the closed boundary defined by flow area A. In examples, conduit system 120 is configured such that central longitudinal axis L intersects flow area A.

In examples, conduit system 120 includes nozzle 140. Nozzle 140 may be configured to provide a flow path from container 106 to conduit lumen 130. Nozzle 140 may be configured to provide a flow path from conduit lumen 130 to container 106. In examples, nozzle 140 is configured to provide a fluid (e.g., purified water) to container 106 to enable mixing of the fluid and a material (e.g., a solid or liquid concentrate) held within container 106. Nozzle 140 may be configured to subsequently provide the mixture to conduit lumen 130 from container 106. In some examples, nozzle 140 is configured to receive a first material (e.g., a solid dialysate concentrate) from first volume 142 of container 106 and a second material (e.g., purified water) from second volume 144 of container 106 and provide a mixture of the first material and second material to conduit lumen 130 For example, nozzle 140 may define a first nozzle inlet 160 configured to receive a flow from container 106 (e.g., from first volume 142). Nozzle 140 may define a second nozzle inlet 162 configured to receive a flow from container 106 (e.g., from second volume 144). Nozzle 140 may be configured to discharge a flow received via first nozzle inlet 160 and/or second nozzle inlet 162 to conduit lumen 130 (e.g., via conduit inlet 156).

In some examples, conduit 126 is configured as a substantially rigid conduit in order to, for example, provide a relatively constant geometry and/or flow path for the discharge of nozzle 140. The relatively constant geometry and/or flow path at the discharge of nozzle 140 may help ensure consistent operation of nozzle 140 when nozzle 140 provides a flow from container 106 to conduit lumen 130, and/or when nozzle 140 provides a flow from conduit lumen 130 to container 106.

For example, the rigidity of conduit 126 may help maintain an orientation of nozzle 140 respect to conduit 126 and/or container 106 to assist a flow symmetry of an inlet jet delivered to container 106 by nozzle 140 to, for example, more effectively direct the inlet jet into a volume defined by container 106 (e.g., a volume holding a concentrate). The rigidity of conduit 126 may limit direct impact of the inlet jet with one or more sides of container 106 defining the volume. In examples, the rigidity of conduit 126 may assist a flow symmetry of the inlet jet within the volume to, for example, enhance dissolution of a concentrate and mixing with a liquid solvent. For example, when conduit system 120 is configured to discharge a fluid vertically (e.g., in a first vertical direction) into the volume defined by container 106, the substantially rigid conduit may be configured to assist in substantially maintaining the inlet jet provided by nozzle 140 in a substantially vertical orientation relative to container 106.

In some examples, the rigidity of conduit 126 may help ensure a relatively consistent pressure ratio across nozzle 140, such that the mixture provided by nozzle 140 is adequately mixed. The rigidity of conduit 126 may help ensure a sufficient venturi effect occurs within nozzle 140, such that a material is sufficiently drawn from container 106 into nozzle 140 (e.g., from first volume 142 through first nozzle 160 and/or from second volume 144 through second nozzle 162). The rigidity of conduit 126 may minimize and/or eliminate unanticipated flow restrictions downstream of nozzle 140 caused by bending and/or kinking that might occur with a substantially flexible conduit between container 106 and machine fluid line 122, such as a flexible tubing.

Conduit wall 128 may define some portion of a boundary of conduit lumen 130. Conduit wall 128 may comprise a substantially inelastic material. In examples, conduit wall 128 is substantially rigid such that conduit wall 128 substantially maintains its shape under the influence of at least its own weight. Conduit wall 128 may have an elasticity less than the elasticity of flexible member 134. In examples, conduit wall 128 is configured such that a force sufficient to deform conduit wall 128 causes a plastic or inelastic deformation of conduit wall 128, and/or a breaking (e.g., a fracture) of conduit wall 128. In examples, flexible member 134 is secured to conduit wall 128 (e.g., an inner surface of conduit wall 128) to cover opening 132, such that when clamp head 136 exerts the clamping force on flexible member 134, flexible member 134 transmits a force to conduit wall 128 as flexible member 134 deforms. Conduit wall 128 may be sufficiently rigid such that conduit wall 128 experiences substantially no deformation when flexible member 134 transmits the force to conduit wall 128. Hence, conduit system 120 may be configured such that conduit 126 provides a relatively constant geometry and/or flow path for the discharge of nozzle 140 while flexible member 134 enables the occlusion of conduit lumen 130 to control a flow from container 106 to machine fluid line 122.

Positioning member 138 is configured to move clamp head 136 between the first and second positions described above. To move clamp head 136 to the second position, positioning member 138 is configured to displace clamp head 136 toward flexible member 134 (e.g., in a direction toward central longitudinal axis L) to cause clamp head 136 to exert the clamping force on flexible member 134. To move clamp head 136 to the first position, positioning member 138 may be configured to displace clamp head 136 away from flexible member 134 (e.g., in a direction away from central longitudinal axis L) to cause clamp head 136 to lessen or substantially cease the clamping force exerted on flexible member 134. For example, positioning member 138 may be configured to displace clamp head 136 in a direction toward central longitudinal axis L to reduce or substantially close the flow area A to reduce or substantially cease a flow through conduit lumen 130. Positioning member 138 may be configured to displace clamp head 136 in a direction away from central longitudinal axis L to increase the flow area A to allow and/or increase a flow through conduit lumen 130. Positioning member 138 may be configured to be manually operable by a user using medical machine 104, such that the user may control a flow of the concentrate from container 106 to machine fluid line 122. In other examples, control circuitry of medical machine 104 or another device is configured to cause positioning member 138 to move clamp head 136 between the first and second positions.

In some examples, positioning member 138 includes a first latching member 168 and a second latching member 170 configured to maintain a clamping force on flexible member 134. First latching member 168 and second latching member 170 may be configured to engage to cause clamp head 136 to maintain the clamping force on flexible member 134. For example, first latching member 168 and second latching member 170 may be configured to mechanically mate, magnetically mate, or engage in some other manner whereby first latching member 168 and second latching member 170 remain substantially stationary with respect to each other. First latching member 168 and second latching member 170 may also be configured to disengage to cause clamp head 136 to reduce or cease exerting the clamping force on flexible member 134. In some examples, first latching member 168 and second latching member 170 may be configured such that a patient or other user may cause the engagement and/or disengagement of first latching member 168 and second latching member 170. First latching member 168 and second latching member 170 may comprise, for example, a stud and a socket (e.g., a snap fastener), a latch and a catch, a barrel bolt and a catch plate, one or more magnets, or any other components configured to form a mated connection with each other.

In examples, conduit system 120 includes control circuitry 172 configured to control positioning member 138. Control circuitry 172 may be configured to receive a control signal (e.g., via communication link 174) and cause positioning member 138 to displace clamp head 136 (e.g., toward or away from central longitudinal axis L) in response to the signal. In examples, control circuitry 172 is configured to receive the control signal from medical machine 104, such as a control signal indicating an out-of-range parameter (e.g., a conductivity, pH, air presence, or another monitored parameter). Control circuitry 172 may cause a displacement of clamp head 136 to substantially commence and/or substantially cease a fluid flow from container 106 based on the control signal. In some examples, control circuitry 172 may be configured to receive the control signal from a user interface 176 configured to be operable by a patient or other user. User interface 176 may have any suitable configuration. For example, user interface 176 can include a button or keypad, a speaker configured to receive voice commands from a user, a display, such as a liquid crystal (LCD), light-emitting diode (LED), or organic light-emitting diode (OLED). User interface 176 may be configured to receive user input, e.g., in the form of pressing one or more buttons on a keypad or via a touch screen. In some examples, user interface 176 may be, include, or otherwise be used in combination with a mobile phone, smartphone, tablet computer, personal computer, desktop computer, personal digital assistant, and/or device configured to provide the control signal to control circuitry 172. In some examples, user interface 176 is mechanically supported by a housing of medical machine 104.

Control circuitry 172, as well as other control circuitry described herein, can comprise one or more microprocessors, digital signal processors (DSPs), application specific integrated circuits (ASICs), field programmable gate arrays (FPGAs), programmable logic circuitry, or the like, either alone or in any suitable combination. In general, processing circuitry or control circuitry described herein may comprise any suitable arrangement of hardware (e.g., circuitry), alone or in combination with software and/or firmware, to perform the various techniques described herein and attributed to the circuitry.

Nozzle 140 may be configured to receive one or more materials from container 106 and provide the one or more materials to conduit lumen 130 (e.g., when conduit system 120 provides a flow from container 106 to medical machine 104). Nozzle 140 may be configured to receive one or more materials from conduit lumen 130 and provide the one or more materials to container 106 (e.g., when conduit system 120 provides a flow from medical machine 104 to container 106). Nozzle 140 may include a nozzle outlet 178 (FIG. 3, FIG. 4) configured to deliver the materials to and/or receive the materials from conduit lumen 130. In examples, nozzle 140 defines a nozzle lumen 180 configured to fluidically couple nozzle outlet 178 with at least one of first nozzle inlet 160 and/or second nozzle inlet 162. Nozzle 140 may be configured to provide a flow in a first direction and provide a flow in a second direction opposite the first direction. For example, nozzle 140 may be configured to provide a flow of the materials from first nozzle inlet 160 and/or second nozzle inlet 162 to nozzle outlet 178 (e.g., when conduit system 120 provides a flow from container 106 to medical machine 104). Nozzle 140 may be configured to provide a flow of the materials from nozzle outlet 178 to first nozzle inlet 160 and/or second nozzle inlet 162 (e.g., when conduit system 120 provides a flow from medical machine 104 to container 106). In examples, nozzle lumen 180 is configured to receive a first material (e.g., a solid or a liquid) from first nozzle inlet 160 and/or a second material (e.g., a solid or a liquid) from second nozzle inlet 162 and provide a mixture of the first material and the second material to nozzle outlet 178. In examples, one of the first material or the second material is a solid solute (e.g., a solid dialysate concentrate) and the other of the first material or the second material is a liquid solvent (e.g., purified water). Nozzle 140 may be configured to provide a solution comprising the solute and the solvent to conduit lumen 130 via nozzle outlet 178. In some examples, nozzle lumen 180 is configured to receive a fluid from conduit lumen 130 via nozzle outlet 178 and direct a discharge of the fluid into container 106 via second nozzle 162 and/or first nozzle 160.

In examples, nozzle lumen 180 defines a nozzle throat 182 configured to accelerate a fluid flow as the fluid flow passes from first nozzle inlet 160 and/or second nozzle 162 to nozzle outlet 178. In examples, an interior surface 184 of nozzle 140 ("nozzle interior surface 184") defines nozzle lumen 180. Nozzle interior surface 184 may define a convergent section wherein a flow area (e.g., a flow area substantially perpendicular to central longitudinal axis L) decreases as the flow area moves from first nozzle inlet 160 and/or second nozzle inlet 162 toward nozzle throat 182. Nozzle interior surface 184 may define a divergent section wherein the flow area increases as the flow area moves from nozzle throat 182 toward nozzle outlet 178. Nozzle 140 may be configured such that the acceleration of the fluid flow as the fluid flow passes through nozzle 140 (e.g., nozzle throat 182) causes a venturi effect (e.g., a suction pressure) acting on at least one of first nozzle inlet 160 or second nozzle 162. Nozzle 140 may be configured such that the venturi effect causes at least one of a first material to be drawn into first nozzle inlet 160 or a second material to be drawn into second nozzle inlet 162 as the fluid flow accelerates through nozzle 140 (e.g., nozzle throat 182).

Nozzle 140 may be secured (e.g., affixed to) to container 106 such that at least one of first nozzle inlet 160 or second nozzle inlet 162 is fluidically coupled to a volume defined by container 106. Nozzle 140 may be secured to container 106 using an adhesive, a mechanical fixture, or some other securing system causing nozzle 140 to mechanically connect to container 106. Container 106 may be configured to hold a material within the defined volume and provide the material to first nozzle inlet 160 and/or second nozzle inlet 162. In examples, nozzle 140 is secured to container 106 such that first nozzle inlet 160 is fluidically coupled to container 106 (e.g., first volume 142) and/or second nozzle inlet 162 is fluidically coupled to container 106 (e.g., second volume 144).

Nozzle 140 may be secured to conduit 126 such that nozzle outlet 178 is fluidically coupled to conduit inlet 156. Nozzle 140 may be secured to conduit 126 using an adhesive, a mechanical fixture, or some other securing system causing nozzle 140 to mechanically connect to conduit 126. For example, nozzle 140 may be configured to engage (e.g., frictionally or mechanically engage) conduit 126 using one or more fittings, such as a coupling, adapter, bushing, slip, slide, or union fitting. As another non-limiting example, nozzle 140 and/or conduit 126 may define screw threads (e.g., screw threads surrounding central longitudinal axis L) with nozzle 140 configured to threadably engage conduit 126 using the screw threads.

Conduit lumen 130 is configured to fluidically couple conduit inlet 156 and conduit outlet 158. In examples, an interior surface 186 of conduit wall 128 ("conduit inner surface 186") defines conduit lumen 130. Conduit wall 128 may include an exterior surface 188 ("conduit exterior surface 188") opposite conduit inner surface 186. Conduit wall 128 defines opening 132 such that opening 132 defines a passage extending from conduit exterior surface 188 to conduit inner wall 186, and such that opening 132 is open to conduit lumen 130. In examples, conduit wall 128 substantially defines an annulus, with conduit inner wall 186 defining an inner surface of the annulus and conduit exterior surface 188 defining an outer surface of the annulus.

Conduit 126 is configured to mechanically support flexible member 134 of flexible member 134. Conduit 126 may mechanically support flexible member 134 such that flexible member 134 covers opening 132 to help prevent egress of fluid (or other material) from inside conduit lumen 130 to an environment outside conduit 126 and to help prevent ingress of fluid (or other material) from the environment outside conduit 126 to conduit lumen 130. Conduit 126 may mechanically support flexible member 134 such that flexible member 134 fluidly isolates flow area A and conduit exterior surface 188. In examples, flexible member 134 is secured to (e.g., affixed to) conduit wall 128. Flexible member 134 may be secured to conduit wall 128 using an adhesive, a mechanical fixture, or some other securing arrangement causing nozzle 140 to substantially attach to conduit wall 128. In examples, flexible member 134 is secured to conduit interior surface 186. In some examples, flexible member 134 may be secured to conduit exterior surface 188. The securing arrangement securing flexible member 134 to conduit wall 128 may be configured to at least partially counter (e.g., react against) stresses imparted to the securing system fluid boundary when clamp head 136 causes a deformation of flexible member 134, such that the flexible member 134 remains secured to conduit interior surface 186 or conduit exterior surface 188 during the deformation.

In examples, conduit 126 mechanically supports flexible member 134 such that flexible member 134 defines at least some portion of flow area A. Flexible member 134 may be configured such that a deformation of flexible member 134 (e.g., by clamp head 136) toward central longitudinal axis L causes flexible member 134 reduce flow area A, such that flexible member 134 substantially occludes conduit lumen 130. In examples, clamp face 190 is configured to contact flexible member 134 to deform member body toward longitudinal axis to cause flexible member 134 to occlude conduit lumen 130 (e.g., reduce the flow area A). Flexible member 134 may be configured to deform substantially elastically, such that when clamp head 136 is withdrawn at least partially through opening 132 (e.g., in a direction away from central longitudinal axis L), flexible member 134 tends to at least partially reverse the deformation to substantially reduce the occlusion (e.g., increase the flow area A).

In examples, flexible member 134 is secured to conduit wall 128 to define at least one fluid boundary (e.g., first fluid boundary B1 and/or a second fluid boundary B2 (FIG. 3, 4)) configured to substantially prevent a flow of fluid through the fluid boundary. In some examples, the securing arrangement substantially defines the fluid boundary. The fluid boundary may be configured to fluidly isolate (e.g., in conjunction with flexible member 134) opening 132 from flow area A. In examples, the fluid boundary is configured to substantially prevent a flow of fluid from conduit lumen 130 through opening 132. The fluid boundary may be configured to fluidly isolate conduit exterior surface 188 and opening 132. In examples, the fluid boundary defines a closed boundary on conduit interior surface 186 or conduit exterior surface 188, such that the fluid boundary defines a closed shape (e.g., circular, oval shaped, polygonal, or some other closed shape). In some examples, the fluid boundary extends around a circumference of conduit lumen 130, such that central longitudinal axis L intersects the closed shape defined by the fluid boundary.

In examples, member lumen 198 is configured to at least partially define the flow path from conduit inlet 156 to conduit outlet 158. Central longitudinal axis L may extend through member lumen 198. In examples, member lumen 198 defines flow area A. In examples, flow area A is a cross-sectional area defined by material lumen 198 (e.g., a cross-sectional area substantially perpendicular to central longitudinal axis L). For example, flexible member 134 may substantially define an annulus (e.g., a tubular body) with member lumen 198 defining an inner passage of the annulus. Clamp head 136 is configured to pass through opening 132 to exert a clamping force on flexible member 134 to cause flexible member 134 to deform inwardly (e.g., toward central longitudinal axis L) and decrease and/or close flow area A.

Figure 4:
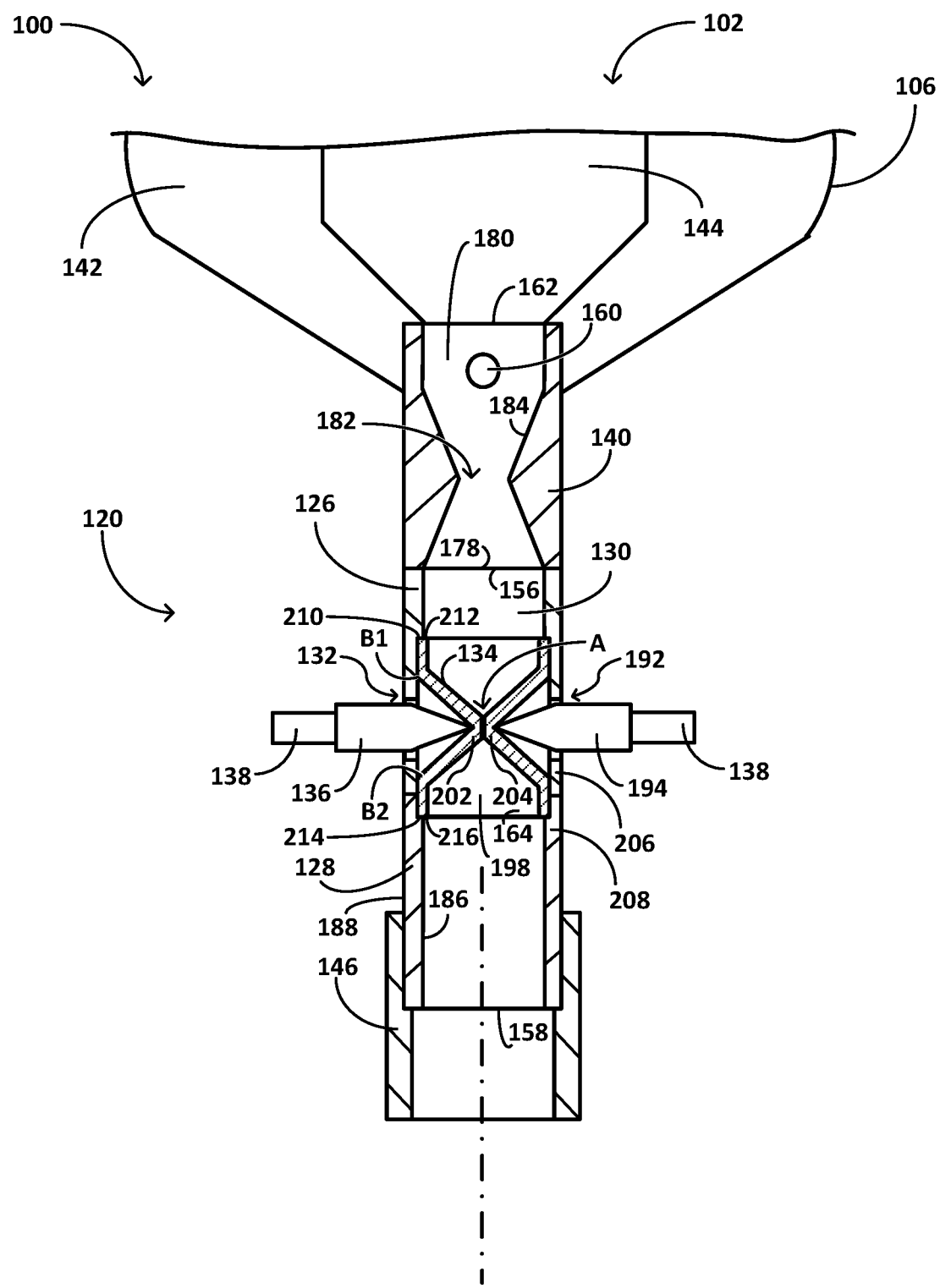
FIG. 4 is a conceptual diagram illustrating a cross-section of the conduit system of FIG. 2 and FIG. 3 with the clamp head in a second position, the cross-section being taken through the central longitudinal axis of the conduit.

Opening 132 is configured to allow at least partial passage of clamp head 136 therethrough. In examples, clamp head 136 includes a clamp face 190 configured to pass through opening 132 to exert a clamping force on flexible member 134, causing flexible member 134 to deform inwardly toward central longitudinal axis L to at least partially occlude conduit lumen 130 (as shown in FIG. 4) (e.g., fully or nearly fully occlude conduit lumen 130). In examples, conduit system 120 is configured to establish clamp head 136 in a first position wherein flexible member 134 is substantially undeformed by a clamping force (e.g., FIG. 3) and a second position wherein flexible member 134 is deformed by a clamping force exerted by clamp head 136 (e.g., FIG. 4). Conduit system 120 may be configured to cause clamp head 136 to move from the first position to the second position, and vice-versa. Conduit system 120 may be configured such that the flow area A decreases when clamp head 136 moves from the first position to the second position. Conduit system 120 may be configured such that the flow area A increases when clamp head 136 moves from the second position to the first position.

In examples, a position of clamp head 136 defines a displacement C (e.g., a distance) between clamp face 190 and central longitudinal axis L. Conduit system 120 may be configured such that a displacement C with clamp head 136 in the first position is greater than a displacement C with clamp head 136 in the second position. In examples, conduit system 120 is configured to decrease the flow area A when clamp head 136 moves in a direction to decrease the displacement C. Conduit system 120 may be configured to increase the flow area A when clamp head 136 moves in a direction to increase the displacement C. Conduit system 120 may be configured to position clamp head 136 to define any displacement C between clamp face 190 and central longitudinal axis L. Hence, conduit system 120 may be configured to define and/or adjust the flow area A based on a position of clamp head 136 relative to conduit 126. Conduit system 120 may be configured to control a flow from conduit inlet 156 to conduit outlet 158 by adjusting the flow area A. For example, conduit system 120 may be configured to decrease flow area A to reduce and/or substantially cease a flow from conduit inlet 156 to conduit outlet 158. Conduit system 120 may be configured to increase flow area A to allow and/or substantially increase a flow from conduit inlet 156 to conduit outlet 158.

In examples, conduit 126 defines at least a second opening 192 configured similarly to opening 132. Second opening 192 can be, for example, longitudinally aligned with opening 132 (along central longitudinal axis L) or longitudinally offset from opening 132 (in which case the longitudinal ends of openings 132, 192 are not aligned). Conduit system 120 may include a second clamp head 194 configured similarly to clamp head 136. For example, conduit system 120 may be configured to displace clamp head 136 at least partially through opening 192 to exert a second clamping force on flexible member 134, causing flexible member 134 to deform inwardly toward central longitudinal axis L. In examples, conduit system 120 (e.g., positioning member 138) is configured to displace second clamp head 194 to cause second clamp head 194 to exert the second clamping force.

Conduit system 120 may be configured to cause second clamp head 194 to exert the second clamping force on flexible member 134 substantially simultaneously with clamp head 136 exerting the first clamping force on flexible member 134. In examples, second clamp head 194 is configured to exert the second clamping force in a direction at least partially opposing the clamping force exerted by clamp head 136. For example, conduit system 120 may be configured to cause clamp head 136 to exert a first clamping force on flexible member 134 in a first direction D1 and cause clamp head 194 to exert a second clamping force on flexible member 134 in a second direction D2. The second direction D1 may define a vector at least partially opposing a vector defined by the first direction D1. In examples, second clamp head 194 is configured to exert the second clamping force in a direction substantially opposite the clamping first exerted by clamp head 136. Conduit system 120 may be configured such that the first clamping force and the second clamping force tend to substantially squeeze flexible member 134 (e.g., FIG. 4) to cause the occlusion of the flow path from conduit inlet 156 to conduit outlet 158. Conduit system 120 may define any number of clamp heads and any number of openings configured similarly to clamp head 136, 194 and opening 132, 192.

Clamp head 136 and second clamp head 194 are each configured to deform flexible member 134 such that flexible member 134 occludes conduit lumen 130 and substantially fluidly isolates conduit inlet 156 from conduit outlet 158. In examples, clamp head 136 and second clamp head 194 are configured to cause a reduction in the flow area A defined by flexible member 134. For example, clamp head 136 and second clamp head 194 may be configured to deform flexible member 134 to substantially collapse member lumen 198 to cause a substantial closure of member lumen 198, such that flexible member 134 substantially fluidly isolates conduit inlet 156 from conduit outlet 158. As another example, clamp head 136 and second clamp head 194 can be configured to substantially trap (e.g., compress) one or more portions of flexible member 134 between clamp face 190 and second clamp face 196 to cause the substantial closure of member lumen 198. For example, clamp head 136 may be configured to deform a first portion 202 of flexible member 134 ("material first portion 202") toward central longitudinal axis L (e.g., in the direction D1). Second clamp head 194 may be configured to deform a second portion 204 of flexible member 134 ("material second portion 204") toward central longitudinal axis L (e.g., in the direction D2). Clamp head 136 and second clamp head 194 may be configured to exert the first clamping force and the second clamping force respectively to cause contact between material first portion 202 and material second portion 204 (e.g., as depicted in FIG. 4). In examples, clamp head 136 and second clamp head 194 are configured to deform flexible member 134 to substantially trap material first portion 202 and material second portion 204 between clamp face 190 and second clamp face 196.

In some examples, clamp face 190 is configured to substantially conform to second clamp face 196 when clamp head 136 and second clamp 194 substantially trap flexible member 134 between clamp face 190 and second clamp face 196. Clamp face 190 substantially conforms to second clamp face 196 such that clamp face 190 and/or second clamp face 196 exert a substantially uniform force profile over a portion of flexible member 134 compressed between clamp face 190 and second clamp face 196.

In some examples, rather than compressing flexible member 134 between clamp faces 190, 196, each clamp head 136, 194 is configured to cause flexible member 134 to compress against conduit 126. For example, clamp head 136 can be configured to trap (e.g., compress) material first portion 202 between clamp face 190 and conduit interior surface 186 to cause a reduction (e.g., a substantial closure) of the flow area A. For example, clamp head 136 may be configured to trap material first portion 202 against a section of conduit interior surface 186 substantially opposite opening 132. Clamp head 136 may be configured to deform first portion 202 toward central longitudinal axis L (e.g., in the direction D1) to cause contact between material first portion 202 and conduit interior surface 186 to trap material first portion 202 against conduit interior surface 186.

In some examples, such as examples in which opening 192 is completely longitudinally offset from opening 132, clamp face 190 is similarly configured to substantially conform to the section of conduit interior surface 186 when clamp head 190 traps flexible member 134 between clamp face 190 and conduit interior surface 186. Clamp face 190 may substantially conform to the section of conduit interior surface 186 such that clamp face 190 exerts a substantially uniform force profile over a respective portion of flexible member 134 when the portion is compressed between clamp face 190 and the section of conduit interior surface 186.

In some examples, conduit 126 has a unibody construction and is formed from one integral piece of material. In other examples, conduit 126 is formed from multiple pieces of material mechanically connected together. For example, conduit 126 may include a first conduit section 206 and a second conduit section 208 configured to fluidically couple with first conduit section 206. Conduit 126 may be configured such that conduit lumen 130 substantially extends through first conduit section 206 and second conduit section 208. In examples, first conduit section 206 defines conduit inlet 156. Second conduit section 208 may define conduit outlet 158. Second conduit section 208 may be configured to fluidically couple with first conduit section 206 such that conduit lumen 130 fluidically couples conduit inlet 156 and conduit outlet 158. In examples, at least one of first conduit section 206 or second conduit section 208 is a substantially rigid conduit section.

In examples, first conduit section 206 is configured to engage (e.g., mechanically and/or frictionally engage) second conduit section 208. Conduit 126 may be configured such that that conduit lumen 130 fluidically couples conduit inlet 156 and conduit outlet 158 when first conduit section 206 engages second conduit section 208. First conduit section 206 may be configured to engage second conduit section 208 using an adhesive, a mechanical fixture, or some other securing system causing first conduit section 206 to substantially attach to second conduit section 208. For example, first conduit section 206 may be configured to engage second conduit 208 using one or more fittings, such as a coupling, adapter, bushing, slip, slide, or union fitting. As another non-limiting example, first conduit section 206 and/or second conduit section 208 may define screw threads (e.g., screw threads surrounding central longitudinal axis L) with first conduit section 206 configured to threadably engage second conduit section 208 using the screw threads.

At least one of first conduit section 206 or second conduit section 208 may be configured to provide at least some degree of mechanical support to flexible member 134. First conduit section 206 and/or second conduit section 208 may be configured to mechanically support flexible member 134 such flexible member 134 defines at least some portion of flow area A. In some examples, first conduit section 206 defines a first step 210 (e.g., a recess) configured to engage (e.g., frictionally engage) a first end 212 of flexible member 134. First step 210 may be configured to abut first end 212 when first step 210 engages first end 212. In examples, first step 210 is configured to conform with first end 212 when first step 210 engages first end 212. Second conduit section 208 may define a second step 214 configured to engage (e.g., frictionally engage) a second end 216 of flexible member 134 opposite first end 212. Second step 214 may be configured to abut second end 216 when second step 214 engages second end 216. In examples, second step 214 is configured to conform with second end 216 when second step 214 engages second end 216. In examples, first step 210 and/or second step 214 may substantially extend around a circumference of conduit 126, such that first step 210 and/or second step 214 substantially surrounds central longitudinal axis L.

First conduit section 206 and/or second conduit section 208 may mechanically support flexible member 134 such that flexible member 134 extends from first conduit section 206 to second conduit section 208. First conduit section 206 and/or second conduit section 208 may mechanically support flexible member 134 such that member lumen 198 fluidically couples first conduit section 206 and second conduit section 208 (e.g., via flow area A). In examples, conduit 126 is configured to provide a method of assembly whereby flexible member 134 is inserted within an initial conduit section (e.g., one of first conduit section 206 or second conduit section 208) such that flexible member 134 extends from the initial conduit section 206. The thus extended portion of flexible member 134 may be inserted within a secondary conduit section (e.g., the other of first conduit section 206 or second conduit section 208), such that flexible member 134 extends from the primary conduit section to the secondary conduit section. In examples, first end 212 contacts first step 210 when flexible member 134 extends from the primary conduit section to the secondary conduit section. Second step 214 may contact second end 216 when flexible member 134 extends from the primary conduit section to the secondary conduit section. Flexible member 134 may substantially cover opening 132 and/or second opening 192 when flexible member 134 extends from the primary conduit section to the secondary conduit section.

In examples, first conduit section 206 defines opening 132 and/or second opening 192. In examples, second conduit section 208 defines opening 132 and/or second opening 192. In some examples, first conduit section 206 defines a first portion of opening 132 and second conduit section 208 defines a second portion of opening 132, and conduit 126 is configured to define opening 132 using the first portion and the second portion when first conduit section 206 engages second conduit section 208. In some examples, first conduit section 206 defines a initial portion of second opening 192 and second conduit section 208 defines a secondary portion of second opening 192, and conduit 126 is configured to define second opening 192 using the initial portion and the secondary portion when first conduit section 206 engages second conduit section 208.

In the example shown in FIG. 3, connector 146 defines conduit outlet 158. Connector 146 may be configured to engage machine connector 148 (FIG. 1) to establish a flow path from first nozzle inlet 160 and/or second nozzle inlet 162 to a lumen defined by machine fluid line 122. In examples, one of connector 146 or machine connector 148 defines a protrusion, and the other of connector 146 or machine connector 148 defines a recess configured to receive the protrusion. For example, connector 146 may define a plug configured to engage a socket defined by machine connector 148. Connector 146 may define a socket configured to engage a plug defined by machine connector 148. Connector 146 may be configured to mechanically couple with machine connector 148 such that a confined fluid path is established from first volume 142 and/or second volume 144 to machine fluid line 122 via nozzle 140, conduit inlet 156, conduit lumen 130, member lumen 198, and/or conduit outlet 158. Connector 146 may be configured to mechanically disengage from machine connector 148 to, for example, separate conduit system 120 and medical machine 104 (FIG. 1).

Connector 146 may be configured to substantially minimize or avoid inadvertent disconnections of connector 146 and machine connector 148, such that the delivery of a fluid from container 106 to medical machine 104 is not unintentionally interrupted. In some examples, connector 146 and/or machine connector 148 includes a mechanical device configured to exert a force on one or more of connector 146 or machine connector 148 tending to help sustain the mechanical engagement of connector 146 and machine connector 148. In some examples, connector 146 and/or machine connector 148 includes a mechanical device and/or magnetic device configured to exert a force on one or more of connector 146 or machine connector 148 that tends to help sustain the mechanical engagement of connector 146 and machine connector 148. The mechanical device and/or magnetic device may be configured to maintain connector 146 substantially stationary relative to machine connector 148 when connector 146 engages machine connector 148.

Connector 146 may be configured to assist in the proper connection of container 106 and medical machine 104 to, for example, help increase the success of an at-home therapies, e.g., dialysis, that require a patient or other user to make connections between a material source and a medical machine. Connector 146 may be configured to help to prevent a patient (or other user) from connecting a material source to the wrong fluid line of medical machine 104. For example, medical machine 104 may include a plurality of machine connectors including machine connector 148, and connector 146 may define a size or a shape such that such that connector 146 may engage only machine connector 148 to fluidically couple conduit lumen 130 and machine fluid line 122. In some examples, connector 146 may include one or more visible indicia to assist in the proper connection of connector 146 and machine connector 148. Connector 146 may include a color and/or include a symbol corresponding to a color and/or symbol, respectively, of machine connector 148 to assist the patient or other user in the proper engagement of connector 146 to medical machine 104.

Control circuitry 172, as well as other control circuitry described herein, can comprise any suitable arrangement of hardware, software, firmware, or any combination thereof, to perform the techniques attributed to conduit system 120 herein. For example, control circuitry 172 may include any one or more microprocessors, digital signal processors (DSPs), application specific integrated circuits (ASICs), field programmable gate arrays (FPGAs), or any other equivalent integrated or discrete logic circuitry, as well as any combinations of such components.

Communication link 174, as well as other communication links described herein, may be hard-line and/or wireless communications links. In some examples, communication link 174 may comprise some portion of control circuitry 172. Communication link 174 may comprise a wired connection, a wireless Internet connection, a direct wireless connection such as wireless LAN, Bluetooth™, Wi-Fi™, and/or an infrared connection. Communication link 174 may utilize any wireless or remote communication protocol.

Figure 5:
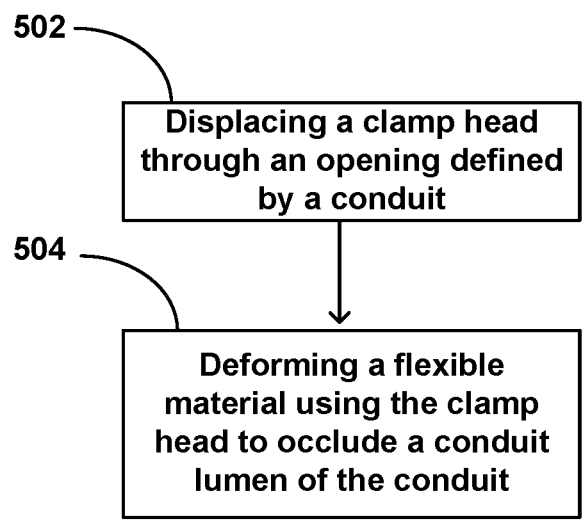
FIG. 5 is a flow diagram of an example technique of using the conduit system.

An example technique for connecting a container with medical machine 104 is illustrated in FIG. 5. Although the technique is described mainly with reference to conduit system 120 of FIGS. 1-4, the technique may be applied to other conduit systems in other examples.

The technique includes displacing a clamp head 136, 194 through a respective opening 132, 192 defined by a conduit 126 (502), the openings 132, 192 extending through conduit wall 128 and opening into conduit lumen 130. Conduit lumen 130 may provide a flow path between container 106 and medical machine 104. Conduit system 120 may cause clamp head 136 to displace through opening 132 in a first direction D1 and cause second clamp head 194 to displace through second opening 192 in a second direction D2 at least partially opposing the first direction D1. In examples, conduit system 120 causes second clamp head 194 to displace through second opening 192 substantially simultaneously with clamp head 136 displacing through opening 132. In examples, clamp head 136, 194 displace through opening 132, 192 in a direction substantially toward central longitudinal axis L defined by conduit 126. Clamp head 136, 194 may displace through opening 132, 192 in a direction substantially away from central longitudinal axis L.

Positioning member 138 may displace clamp head 136, 194 through opening 132, 192 in a direction toward or in a direction away from central longitudinal axis L. Positioning member 138 may be operated by a patient using medical machine 104 or another user assisting the patient, such that the patient or other user may cause the displacement of clamp head 136, 194 through opening 132, 192. In examples, conduit system 120 controls positioning member 138 using control circuitry 172. Control circuitry 172 may receive a control signal (e.g., via communication link 174) and cause positioning member 138 to displace clamp head 136, 194 in response to the signal. In examples, control circuitry 172 receives the control signal from medical machine 104. In examples, control circuitry 172 receives the control signal from a user interface 176 based on an input from a patient or other user.

Positioning member 138 may cause first latching member 168 and a second latching member 170 to engage to cause clamp head 136, 194 remain displaced through opening 132, 192. First latching member 168 and second latching member 170 may mechanically mate, magnetically mate, or engage in some other manner whereby first latching member 168 and second latching member 170 remain substantially stationary with respect to each other. First latching member 168 and second latching member 170 may disengage to enable displacement of clamp head 136, 194 to through opening 132, 192 in a direction substantially away from central longitudinal axis L. First latching member 168 and second latching member 170 may be engaged and/or disengaged by a patient or other user to cause the displacement of clamp head 136, 194 through opening 132, 192.

The technique includes deforming flexible member 134 using clamp head 136, 194 to occlude conduit lumen 130 (504). Flexible member 134 may substantially cover opening 132, 194 such that clamp head 136, 194 causes a deformation of flexible member 134 when clamp head 136, 194 displaces through opening 132, 192. Flexible member 134 may substantially prevent a fluid flow passing from conduit lumen 130 through opening 132, 192 as clamp head 136, 194 deforms of flexible member 134. Clamp head 136, 194 may exert one or more clamping forces on flexible member 134 to deform flexible member 134. In examples, clamp head 136, 194 moves from a first position substantially outside conduit 126 to second position displaced through opening 132, 196 to exert the one or more clamping forces on flexible member 134. In examples, clamp head 136 exerts a first clamping force on flexible member 134 (e.g., substantially in the first direction D1) and second clamp head 194 exerts a second clamping force on flexible member 134 (e.g., substantially in the second direction D2) opposing the first clamping force. In examples, clamp head 136 contact flexible member 134 using clamp face 190 to exert the first clamping force. Second clamp head 194 may use clamp face 196 to exert the second clamping force on flexible member 134.

Flexible member 134 may reduce and/or prevent a fluid flow through conduit lumen 130 when clamp head 136, 194 causes the deformation of flexible member 134. Flexible member 134 may at least partially define some portion of a flow area defined within conduit lumen 130, such that the deformation of flexible member 134 (e.g., toward central longitudinal axis L) decreases flow area A to occlude the flow path within conduit lumen 130. In examples, flexible member 134 defines member lumen 198 defining flow area A. The displacement of clamp head 136, 192 through opening 132, 192 may deform flexible member 134 toward central longitudinal axis L to cause a reduction or substantial closure of flow area A defined by member lumen 198. In examples, displacement of clamp head 136, 192 through opening 132, 192 may cause a movement of flexible member 134 away from central longitudinal axis L to cause an increase in flow area A defined by member lumen 198.

Nozzle 140 may provide a fluid flow to conduit lumen 130. In examples, nozzle 140 receives the fluid flow from container 106 and provides the fluid flow to conduit lumen 130. In examples, nozzle 140 receives the fluid flow from conduit lumen 130 and provides the fluid flow to container 106. In examples, nozzle 140 receives a fluid (e.g., purified water) from conduit lumen 130 and provides the fluid to container 106 to generate a mixture between the fluid and a concentrate (e.g., a solid or liquid concentrate) held within container 106. Nozzle 140 may receive the mixture from container 106 and provide the mixture to conduit lumen 130. In examples, nozzle 140 receives a first material (e.g., a solid dialysate concentrate) and a second material (e.g., purified water) from container 106 and causes mixing of the first material and the second material before proving the first material and the second material to conduit lumen 130. In examples, nozzle 140 receives the first material via first nozzle inlet 160 from first volume 142 of container 106. Nozzle 140 may receive the second material via second nozzle inlet 162 from second volume 144 of container 106. Nozzle 140 may discharge a mixture of the first material and the second material into a relatively constant geometry and/or flow path defined by conduit 126 to, for example, help ensure the mixture provided by nozzle 140 is adequately mixed.

Connector 146 may fluidically couple conduit lumen 130 and machine fluid line 122. Connector 146 may engage machine connector 148 to fluidically couple conduit lumen 130 and machine fluid line 122. Medical machine 104 may mechanically support machine connector 148. In examples, connector 146 mechanically disengages from machine connector 148 to separate conduit system 120 and medical machine 104. Fluid connector 150 may fluidically couple machine fluid line 116 and container 106. Fluid connector 150 may engage fluid line connector 154 to fluidically couple machine fluid line 116 and container 106. Fluid connector 150 may mechanically disengage from fluid line connector 154 to separate container system 105 and machine fluid line 116.

The present disclosure includes the following examples.

Example 1: An apparatus comprising: a conduit comprising a conduit wall defining a conduit lumen, wherein the conduit wall defines an opening open to the conduit lumen; a flexible member secured to the conduit wall, wherein the flexible member covers the opening, and wherein the flexible member is configured to deform to occlude the conduit lumen when a clamping force in a direction toward conduit lumen is exerted on the flexible member; and a clamp head configured to pass through the opening to exert the clamping force on the flexible member.

Example 2: The apparatus of example 1, wherein the conduit lumen extends from a conduit inlet defined by the conduit to a conduit outlet defined by the conduit, the apparatus further comprising a nozzle mechanically engaged with the conduit inlet, wherein the nozzle defines a nozzle throat in fluid communication with the conduit inlet, and wherein the nozzle throat is configured to cause mixing of a medical solution received by the conduit lumen.

Example 3: The apparatus of example 1 or example 2, wherein the nozzle is secured to a container configured to hold one or more materials, and wherein the nozzle is configured to provide fluid communication from the container to the conduit inlet.

Example 4: The apparatus of any of examples 1-3, wherein the conduit lumen extends from a conduit inlet defined by the conduit to a conduit outlet defined by the conduit, wherein the flexible member at least partially defines a member lumen configured to provide fluid communication between the conduit inlet and the conduit outlet, and wherein the flexible member is configured to occlude the conduit lumen by at least deforming to reduce a flow area defined by the member lumen when the clamp head exerts the clamping force on the flexible member.

Example 5: The apparatus of any of examples 1-4, wherein the flexible member is secured to an interior surface of the conduit wall.

Example 6: The apparatus of any of examples 1-5, wherein the flexible member is secured to an exterior surface of the conduit wall.

Example 7: The apparatus of any of examples 1-6, wherein the conduit lumen extends from a conduit inlet defined by the conduit to a conduit outlet defined by the conduit, and wherein the conduit includes a rigid body configured such that the conduit inlet, the conduit outlet, and the opening are substantially stationary with respect to each other when the clamp head exerts the clamping force to deform the flexible member.

Example 8: The apparatus of any of examples 1-7, wherein the conduit lumen extends from a conduit inlet defined by the conduit to a conduit outlet defined by the conduit, wherein the flexible member defines at least some portion of a flow area configured to provide fluid communication between the conduit inlet and the conduit outlet through the flow area, and wherein the flexible member is configured to decrease the flow area when the flexible member deforms to occlude the conduit lumen.

Example 9: The apparatus of any of examples 1-8, further comprising a positioning member configured to displace the clamp head, wherein the positioning member includes a first latching member configured to engage a second latching member, and wherein the positioning member is configured to maintain a position causing the clamp head to exert the clamping force when the first latching member mates with the second latching member.

Example 10: The apparatus of any of examples 1-9, wherein the conduit is configured to engage a fluid line of a medical machine to deliver a medical solution to the medical machine.

Example 11: The apparatus of example 10, further comprising a nozzle mechanically engaged with the conduit, wherein the nozzle is configured to provide the medical solution from a container, wherein the medical solution comprises a solvent and a solute, and wherein the nozzle is configured to cause mixing of the solvent and the solute.

Example 12: The apparatus of any of examples 1-11, wherein the clamp head is a first clamp head and the opening includes a first opening, the apparatus further comprising a second clamp head, wherein the conduit wall defines a second opening, wherein the flexible member covers the second opening, and wherein the second clamp head is configured to pass through the second opening to exert a second clamping force on the flexible member.

Example 13: The apparatus of example 12, further comprising a positioning member configured to displace the first clamp head and the second clamp head toward the flexible member to deform the flexible member.

Example 14: The apparatus of example 12 or example 13, wherein the second clamp head is configured to exert the second clamping force in a direction opposing the clamping force exerted by the first clamp head.

Example 15: The apparatus of any of examples 1-14, wherein the conduit includes: a first conduit section defining a conduit inlet; and a second conduit section defining a conduit outlet; wherein an end of the first conduit section opposite the conduit inlet is configured to engage an end of the second conduit section opposite the conduit outlet to define the conduit lumen, and wherein the flexible member extends from the first conduit section to the second conduit section.

Example 16: A fluid delivery system comprising: a container defining a volume; a nozzle defining a nozzle throat in fluid communication with the volume; a conduit comprising a conduit wall defining a conduit lumen extending from a conduit inlet to a conduit outlet, wherein the nozzle throat is in fluid communication with the conduit inlet, and wherein the conduit wall defines an opening open to the conduit lumen; a flexible member secured to the conduit wall, wherein the flexible member covers the opening, and wherein the flexible member is configured to deform to occlude the conduit lumen; and a clamp head configured to pass through the opening to exert a clamping force on the flexible member to cause the flexible member to deform to occlude the conduit lumen, wherein the conduit includes a rigid body configured such that the conduit inlet, the conduit outlet, and the conduit wall defining the opening are substantially stationary with respect to each other when the clamp head exerts the clamping force on the flexible member.

Example 17: The apparatus of example 16, wherein the flexible member defines at least some portion of a flow area configured to provide fluid communication between the conduit inlet and the conduit outlet through the flow area, and wherein the flexible member is configured to decrease the flow area when the flexible member deforms to occlude the conduit lumen.

Example 18: The apparatus of example 16 or example 17, further comprising a positioning member configured to displace the clamp head, wherein the positioning member includes a first latching member configured to engage a second latching member, and wherein the positioning member is configured to maintain a position causing the clamp head to exert the clamping force when the first latching member engages the second latching member.

Example 19: A method, comprising: displacing a clamp head through an opening defined by a conduit wall of a conduit, wherein the conduit wall defines a conduit lumen and the opening opens into the conduit lumen; exerting a clamping force on a flexible member covering the opening using the clamp head displaced through the opening, the clamping force being sufficient to deform the flexible member to occlude the conduit lumen.

Example 20: The method of example 19, further comprising: providing the fluid flow from a nozzle to the conduit lumen.

Various examples of the disclosure have been described. Any combination of the described systems, operations, or functions is contemplated. These and other examples are within the scope of the following claims.

What is claimed is:

1. An apparatus comprising:
   a medical bag defining a volume;
   a nozzle secured to the medical bag, the nozzle including a nozzle inlet, a nozzle outlet, and at least one of a convergent section or a divergent section between the nozzle inlet and the nozzle outlet, wherein the nozzle inlet is configured to receive a fluid flow from the volume;
   a rigid conduit supporting the nozzle, the rigid conduit comprising a conduit wall defining a conduit lumen extending from a conduit inlet defined by the rigid conduit to a conduit outlet defined by the rigid conduit, wherein the conduit wall defines an opening open to the conduit lumen, wherein the nozzle outlet is configured to discharge the fluid flow from the volume through the conduit inlet to the conduit lumen as the rigid conduit supports the nozzle;

a flexible member secured to the conduit wall, wherein the flexible member covers the opening, and wherein the flexible member is configured to deform to occlude the conduit lumen between the conduit inlet and the conduit outlet when a clamping force in a direction toward conduit lumen is exerted on the flexible member; and a clamp head configured to pass through the opening to exert the clamping force on the flexible member.

2. The apparatus of claim 1, wherein the nozzle is mechanically engaged with the conduit inlet.

3. The apparatus of claim 1, wherein the flexible member at least partially defines a member lumen configured to provide fluid communication between the conduit inlet and the conduit outlet, and wherein the flexible member is configured to occlude the conduit lumen by at least deforming to reduce a flow area defined by the member lumen when the clamp head exerts the clamping force on the flexible member.

4. The apparatus of claim 1, wherein the flexible member is secured to an interior surface of the conduit wall.

5. The apparatus of claim 1, wherein the flexible member is secured to an exterior surface of the conduit wall.

6. The apparatus of claim 1, wherein the conduit includes a rigid body configured such that the conduit inlet, the conduit outlet, the opening, and the nozzle are substantially stationary with respect to each other when the clamp head exerts the clamping force to deform the flexible member.

7. The apparatus of claim 1, wherein the flexible member defines at least some portion of a flow area configured to provide fluid communication between the conduit inlet and the conduit outlet through the flow area, and wherein the flexible member is configured to decrease the flow area when the flexible member deforms to occlude the conduit lumen.

8. The apparatus of claim 1, further comprising a positioning member configured to displace the clamp head,
wherein the positioning member includes a first latching member configured to engage a second latching member, and
wherein the positioning member is configured to maintain a position causing the clamp head to exert the clamping force when the first latching member mates with the second latching member.

9. The apparatus of claim 1, wherein the conduit is configured to engage a fluid line of a medical machine to deliver a medical solution to the medical machine.

10. The apparatus of claim 9,
wherein the nozzle is configured to receive the medical solution from the medical bag,
wherein the medical solution comprises a solvent and a solute, and
wherein the nozzle is configured to cause mixing of the solvent and the solute.

11. The apparatus of claim 1, wherein the clamp head is a first clamp head and the opening includes a first opening, the apparatus further comprising a second clamp head,
wherein the conduit wall defines a second opening,
wherein the flexible member covers the second opening, and
wherein the second clamp head is configured to pass through the second opening to exert a second clamping force on the flexible member.

12. The apparatus of claim 11, further comprising a positioning member configured to displace the first clamp head and the second clamp head toward the flexible member to deform the flexible member.

13. The apparatus of claim 11, wherein the second clamp head is configured to exert the second clamping force in a direction opposing the clamping force exerted by the first clamp head.

14. The apparatus of claim 1, wherein the conduit includes:
a first conduit section defining the conduit inlet; and
a second conduit section defining the conduit outlet,
wherein an end of the first conduit section opposite the conduit inlet is engaged with an end of the second conduit section opposite the conduit outlet to define the conduit lumen, and
wherein the flexible member extends from the first conduit section to the second conduit section.

15. A fluid delivery system comprising:
a medical bag defining a volume;
a nozzle secured to the medical bag, the nozzle defining a nozzle throat, a nozzle inlet, a nozzle outlet, and at least one of a convergent section between the nozzle inlet and the nozzle throat or a divergent section between the nozzle throat and the nozzle outlet, wherein the nozzle inlet is configured to receive a fluid flow from the volume;
a rigid conduit supporting the nozzle, the rigid conduit comprising a conduit wall defining a conduit lumen extending from a conduit inlet defined by the rigid conduit to a conduit outlet defined by the rigid conduit,
wherein the nozzle throat is in fluid communication with the conduit inlet,
wherein the nozzle outlet is configured to discharge the fluid flow from the volume through the conduit inlet to the conduit lumen as the rigid conduit supports the nozzle, and
wherein the conduit wall defines an opening open to the conduit lumen;
a flexible member secured to the conduit wall, wherein the flexible member covers the opening, and wherein the flexible member is configured to deform to occlude the conduit lumen between the conduit inlet and the conduit outlet; and
a clamp head configured to pass through the opening to exert a clamping force on the flexible member to cause the flexible member to deform the conduit lumen, wherein the rigid conduit is configured such that the conduit inlet, the conduit outlet, the conduit wall, and the nozzle are substantially stationary with respect to each other when the clamp head exerts the clamping force on the flexible member.

16. The fluid delivery system of claim 15, wherein the flexible member defines at least some portion of a flow area configured to provide fluid communication between the conduit inlet and the conduit outlet through the flow area, and wherein the flexible member is configured to decrease the flow area when the flexible member deforms to occlude the conduit lumen.

17. The fluid delivery system of claim 15, further comprising a positioning member configured to displace the clamp head,
wherein the positioning member includes a first latching member configured to engage a second latching member, and wherein the positioning member is configured to maintain a position causing the clamp head to exert the clamping force when the first latching member engages the second latching member.

18. A method, comprising:

receiving, by a nozzle secured to a medical bag and supported by a rigid conduit, a fluid flow from a volume defined by the medical bag to a nozzle inlet defined by the nozzle, the nozzle defining a nozzle outlet and at least one of a convergent section or a divergent section between the nozzle inlet and the nozzle outlet;

discharging, by the nozzle, the fluid flow from the nozzle outlet through a conduit inlet defined by the rigid conduit into a conduit lumen defined by the rigid conduit, the conduit lumen extending from the conduit inlet to a conduit outlet defined by the rigid conduit;

displacing a clamp head through an opening defined by a conduit wall of the rigid conduit, wherein the opening opens into the conduit lumen; and exerting a clamping force on a flexible member covering the opening and secured to the conduit wall using the clamp head displaced through the opening, the clamping force being sufficient to deform the flexible member to occlude the conduit lumen between the conduit inlet and the conduit outlet.

19. The apparatus of claim 1, wherein the volume is a first volume and the medical bag includes a second volume fluidically isolated from the first volume, wherein the nozzle includes a first nozzle inlet fluidically connecting the first volume and one of the convergent section or the divergent section, and wherein the nozzle includes a second nozzle inlet fluidically connecting the second volume and one of convergent section or the divergent section.

20. The method of claim 18, further comprising decreasing, by the flexible member, a flow area when the flexible member deforms to occlude the conduit lumen.

\* \* \* \* \*